United States Patent
Hiraki et al.

(10) Patent No.: US 6,355,259 B1
(45) Date of Patent: Mar. 12, 2002

(54) COSMETIC COMPOSITION FOR SKIN COMPRISING UREA

(75) Inventors: Yoshio Hiraki; Satoshi Yoshikawa; Gonichi Tagami; Yasuyuki Takahashi, all of Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 09/210,767

(22) Filed: Dec. 14, 1998

(30) Foreign Application Priority Data

Dec. 15, 1997 (JP) ............................................ 9-362527

(51) Int. Cl.$^7$ ................................................. A61K 7/48
(52) U.S. Cl. ........................ 424/401; 514/845; 514/846; 514/847; 514/944
(58) Field of Search ........................ 424/401; 514/845, 514/846, 847, 944

(56) References Cited

U.S. PATENT DOCUMENTS 5,213,799 A * 5/1993 Goring et al.

FOREIGN PATENT DOCUMENTS

JP 51-48441 4/1976
JP 52-109487 9/1977

OTHER PUBLICATIONS

Copy of registry file disodium hydrogen phosphate from STN Express (2000).*
Chemical Abstracts, vol. 127, No. 13, Sep. 29, 1997, AN 180929, JP 09 175983, Jul. 8, 1997.
Derwent Publications, AN 1980–19363C, JP 55 015901, Feb. 4, 1980.
Derwent Publications, AN 1986–199655, JP 61 130204, Jun. 18, 1986.
Derwent Publications, AN 1976–44587X, JP 51 048441, Apr. 26, 1976.

* cited by examiner

*Primary Examiner*—Diana Dudash
*Assistant Examiner*—Alysia Berman
(74) *Attorney, Agent, or Firm*—Oblon, Spivak, McClelland, Maier & Neustadt, P.C.

(57) ABSTRACT

A cosmetic composition for skin use which comprises urea and a buffer comprising disodium hydrogenphosphate and citric acid or a buffer comprising potassium dihydrogenphosphate and disodium hydrogenphosphate, or both, and a cosmetic composition further comprising allantoin. Notwithstanding inclusion of urea which is useful for preventing rough dry skin and maintaining moisturization, the cosmetic composition does not have problems such as an increase in pH and an odor from ammonia produced by urea during storage for a long period of time.

3 Claims, No Drawings

COSMETIC COMPOSITION FOR SKIN COMPRISING UREA

BACKGROUND OF THE INVENTION

1. Field of the Invention

The present invention relates to a cosmetic composition for skin comprising urea which is useful for preventing rough dry skin and maintaining moisturization. The cosmetic composition for skin of the present invention is characterized by the capability of suppressing odor from ammonia produced by urea during storage.

2. Description of the Background Art

Significance of a natural moisturizing factor (NMF) which is present in keratinous cells and a sebum cutaneum membrane which covers the skin in naturally maintaining the skin has conventionally been known. If these do not function properly, the moisture content of the skin decreases, resulting in dry and rough skin.

For this reason, various additives which supplement the above-mentioned functions, for example, polyhydric alcohols such as glycerol and propylene glycol, saccharides such as sorbitol and maltitol, amino acids, macromolecule compounds such as hyaluronic compounds and chondroitin acid, and lactic acid bacterium culture supernatant liquid, have conventionally been added to cosmetic compositions for skin.

Urea is known to exhibit various physiological functions and has been used very often in cosmetic compositions. Moisture retention activity of keratin, cell activation function, antibacterial action, antipruritic function, and the like are given as the functions of urea. Urea is thus added to cosmetic compositions and drug compositions with the object of preventing skin chapping and retaining moisture.

However, urea in the compositions decomposes into ammonia and carbon dioxide during storage, increasing the pH and generating an unacceptable ammonia odor.

Various methods have been proposed to solve this problem. For example, Japanese Patent Application Laid-open No. 109487/1977 discloses that the addition of allantoin in an amount of 1 wt % or more for the amount of urea stabilizes urea and can suppress ammonia odor. The technologies which attain the same effect include, for example, a method of adding a buffer to urea to adjust the pH to 6–9 and further adding an ammonium salt, allantoin, an allantoin derivative, or uric acid (Japanese Patent Application Laid-open No. 48441/1976), a method of adding a basic amino acid to urea (Japanese Patent Application Laid-open No. 30509/1986), a method of adding taurine to urea (Japanese Patent Publication No. 81567/1992), a method of adding a neutral amino acid, acidic amino acid, or alkaline salt of an acidic amino acid (Japanese Patent Publication No. 56002/1992), and a method of adding lecitin to urea (Japanese Patent Publication No. 31541/1993, Japanese Patent Application Laid-open No. 364104/1992).

These methods are not always satisfactory in stabilizing urea or in suppressing ammonia odor due to generation of ammonia over time.

Therefore, an object of the present invention is to provide a cosmetic composition comprising urea useful for preventing skin chapping and retaining skin moisture, which does not exhibit a pH increase and generation of an ammonia odor during storage for a long period of time.

The present inventors have conducted extensive studies to obtain a composition incorporating urea in a stable manner. As a result, the inventors have found that the capability of a composition to incorporate urea in a stable manner depends not only on the pH, but also largely on a buffer constituting the system of a composition such as a cosmetic composition. The inventors have further found that a cosmetic composition in which the above-mentioned problems are solved can be obtained by appropriately selecting and using a specific buffer and that, if allantoin is added, a cosmetic composition in which decomposition of urea is suppressed even more can be obtained. These findings have led to the completion of the present invention.

SUMMARY OF THE INVENTION

The above object is attained in the present invention by the provision of a cosmetic composition for skin use which comprises (i) urea and (ii) a buffer comprising disodium hydrogenphosphate and citric acid or a buffer comprising potassium dihydrogenphosphate and disodium hydrogenphosphate, or both.

In a preferred embodiment of the present invention, the above cosmetic composition for skin use further comprises allantoin.

Other objects, features and advantages of the invention will hereinafter become more readily apparent from the following description.

DETAILED DESCRIPTION OF THE INVENTION AND PREFERRED EMBODIMENTS

Urea is the major NMF component in the cosmetic composition for skin use of the present invention and is incorporated preferably in an amount up to about 5 w/w % (hereinafter indicated as "%").

The other component which is a buffer comprising disodium hydrogenphosphate and citric acid or a buffer comprising potassium dihydrogenphosphate and disodium hydrogenphosphate (hereinafter called "specific buffer") is incorporated with urea to improve stability of the composition over time. It is possible to use either the disodium hydrogenphosphate-citric acid buffer or the potassium dihydrogenphosphate-disodium hydrogenphosphate buffer, or a combination of both buffers. The amount of the specific buffer to be added should be in the range from 10 to 70%, preferably from 20 to 50%, of the amount of urea. If the amount of the specific buffer is more than 50%, the salt concentration is so high that the resulting cosmetic composition may irritate the skin. In addition, when the composition with a high content of specific buffer is in the form of emulsion such as a milky lotion, the emulsion tends to break.

Use of a buffer to stabilize the pH of cosmetic compositions is widely known. Incorporation of a buffer in a cosmetic composition comprising urea is also known. However, the remarkable stabilizing effect of the above specific buffers as compared with other conventional buffers has not been known in the art. The effect has been found for the first time by the inventors of the present invention. Specifically, other buffers which are commonly used for cosmetic compositions such as a citric acid-sodium hydroxide buffer or a PCA-sodium PCA buffer cannot sufficiently stabilize pH or suppress odor.

The urea-containing cosmetic composition for skin use of the present invention in which a specific buffer is used in combination with urea exhibits an excellent pH stabilizing effect and a superb ammonia odor suppressing effect. However, even a slight ammonia odor may significantly affect the product quality of some cosmetic compositions. Such an odor must be completely suppressed.

In such a case, the use of allantoin can more effectively suppress the ammonia odor. However, of the two specific buffers mentioned above only the disodium hydrogenphosphate-citric acid buffer can suppress the ammonia odor when used in combination with the allantoin. No appreciable effect can be achieved when allantoin is used in combination with another specific buffer, the potassium dihydrogenphosphate-disodium hydrogenphosphate buffer.

The other buffers may or may not suppress the generation of ammonia when used together with allantoin. For example, the combined use of allantoin with a PCA-sodium PCA buffer is not only ineffective in suppressing the ammonia odor, but rather accelerates generation of ammonia odor. In addition, the combined use of allantoin does not significantly affect the capability of a buffer to stabilize pH, nor is the independent use of allantoin effective for suppressing the ammonia odor.

The ammonia odor suppressing effect achieved by the combined use of allantoin is thus not always due to the pH stabilization effect. Although the reason for this effect is not necessarily clear, a synergistic effect of the disodium hydrogenphosphate-citric acid buffer and allantoin is a possible reason.

Although there are no specific limitations to the amount of allantoin, the use of 1% or more of the amount of urea is sufficient for suppressing the ammonia odor, when the allantoin is used in combination with the specific buffer of the present invention.

The amount of the disodium hydrogenphosphate-citric acid buffer used in combination with allantoin is preferably in the range from about 10 to 70%, and more preferably from about 20 to 50%, of the amount of urea.

The initial pH of the urea-containing cosmetic composition for skin use of the present invention prepared by formulating the above-mentioned components is preferably from pH 4.5 to pH 6.5.

The urea-containing cosmetic composition for skin use of the present invention can be prepared by homogeneously mixing the above-described components. The composition can be made into various forms such as a liquid preparation, milky lotion, cream, gel preparation, and the like. Various additives such as, for example, whey (2), sodium hyaluronate, and lamella structure lipid, can optionally be incorporated depending on the form of the preparation inasmuch as the effect of the present invention is not adversely affected.

The urea-containing cosmetic composition for skin use of the present invention can prevent rough dry skin due to urea and can provide a moisturizing effect. At the same time, the cosmetic composition can suppress generation of an ammonia odor originating from urea during storage, particularly, under high temperature conditions. The present invention has thus increased the commercial value of the urea-containing cosmetic composition for skin use.

Other features of the invention will become apparent in the course of the following description of the exemplary embodiments which are given for illustration of the invention and are not intended to be limiting thereof.

EXAMPLES

Experimental Example 1
<Urea Stabilization Capability According to Type of Buffer>

Four urea solutions were prepared using different buffers to examine the pH stability and generation of ammonia odor according to the following method. The effect of each buffer on the urea stability over time was determined based on the results. The results are shown in Tables 1 to 4.

(1) Buffers Used
  (Buffer 1) Disodium hydrogenphosphate-citric acid
  (Buffer 2) Potassium dihydrogenphosphate-disodium hydrogenphosphate
  (Buffer 3) Citric acid-sodium hydroxide
  (Buffer 4) PCA-sodium PCA (2) Preparation of Urea Solutions

| | |
|---|---|
| Urea | 5.0% |
| Buffer | 2.0% |
| 1,3-Butylene glycol | 3.0% |
| Methyl paraoxybenzoate | 0.1% |
| Ion exchanged water | Balance |
| pH | 6.0 |

(3) Confirmation of pH Change and Odor Generation

The stability over time of each urea solution prepared in (2) above was confirmed. Specifically, each solution was filled into a glass bottle and stored in a thermostat at 40° C. or 50° C. Samples were collected at 2 and 4 weeks to measure the pH.

In addition, generation of urea odor from each solution was organoleptically evaluated by five expert panelists. When the organoleptic evaluation was difficult, ammonia was analyzed using an ammonia detector tube. The results were used as references.

The pH change was indicated by the difference in the pH values (Δ pH). Generation of odor was evaluated according to the following standard.

Odor Evaluation Standard
  A: No odor at all
  B: Slight odor
  C: A little odor
  D: Easily appreciable odor
  E: Conspicuous odor (4) The Results The pH changes when stored at 40° C. and 50° C. are respectively shown in Tables 1 and 2. The results of odor generation evaluation at 40° C. and 50° C. are shown in Tables 3 and 4.

TABLE 1

| | pH change when stored at 40° C. (Δ pH) | |
|---|---|---|
| Buffer used | After 2 weeks | After 4 weeks |
| Buffer 1 | 0.33 | 0.60 |
| Buffer 2 | 0.40 | 0.60 |
| Buffer 3 | 0.76 | 1.82 |
| Buffer 4 | 2.08 | 2.16 |

TABLE 2

| | pH change when stored at 50° C. (Δ pH) | |
|---|---|---|
| Buffer used | After 2 weeks | After 4 weeks |
| Buffer 1 | 0.94 | 1.48 |
| Buffer 2 | 0.85 | 1.21 |
| Buffer 3 | 2.45 | 2.79 |
| Buffer 4 | 2.71 | 2.75 |

TABLE 3

| | Ammonia odor when stored at 40° C. | |
|---|---|---|
| Buffer used | After 2 weeks | After 4 weeks |
| Buffer 1 | A | A |
| Buffer 2 | A | A |
| Buffer 3 | A | A |
| Buffer 4 | A | B |

TABLE 4

| | Ammonia odor when stored at 50° C. | |
|---|---|---|
| Buffer used | After 2 weeks | After 4 weeks |
| Buffer 1 | A ~ B | A ~ B |
| Buffer 2 | A | A ~ B |
| Buffer 3 | A ~ B | E |
| Buffer 4 | B | C |

As a result of the above experiment, both the pH stability and the ammonia odor suppression effect are excellent when a disodium hydrogenphosphate-citric acid buffer or a potassium dihydrogenphosphate-disodium hydrogenphosphate buffer was used.

Experimental Example 2
<Urea Stabilization Capability According to Type of Buffer in which Allantoin is Used>

Using the same four buffers as in Experimental Example 1, urea solutions in which allantoin is used in combination were prepared. The pH stability and generation of ammonia odor were examined in the same manner as in Experimental Example 1. The effect of each buffer on the urea stability over time was determined based on the results The results are shown in Tables 5 to 8.

(1) Preparation of Urea Solutions

| | |
|---|---|
| Urea | 5.0% |
| Allantoin | 0.2% |
| Buffer | 2.0% |
| 1,3-Butylene glycol | 3.0% |
| Methyl paraoxybenzoate | 0.1% |
| Ion exchanged water | Balance |
| pH | 6.0 |

(2) The Results

The pH changes when stored at 40° C. and 50° C. are respectively shown in Tables 5 and 6. The results of odor generation evaluation at 40° C. and 50° C. are shown in Tables 7 and 8.

TABLE 5

| | pH change when stored at 40° C. (Δ pH) | |
|---|---|---|
| Buffer used | After 2 weeks | After 4 weeks |
| Buffer 1 | 0.35 | 0.62 |
| Buffer 2 | 0.38 | 0.56 |
| Buffer 3 | 0.73 | 1.51 |
| Buffer 4 | 1.73 | 1.62 |

TABLE 6

| | pH change when stored at 50° C. (Δ pH) | |
|---|---|---|
| Buffer used | After 2 weeks | After 4 weeks |
| Buffer 1 | 0.96 | 1.45 |
| Buffer 2 | 0.91 | 1.19 |
| Buffer 3 | 2.09 | 2.51 |
| Buffer 4 | 2.16 | 2.38 |

TABLE 7

| | Ammonia odor when stored at 40° C. | |
|---|---|---|
| Buffer used | After 2 weeks | After 4 weeks |
| Buffer 1 | A | A |
| Buffer 2 | A | A |
| Buffer 3 | A | A |
| Buffer 4 | A | A |

TABLE 8

| | Ammonia odor when stored at 50° C. | |
|---|---|---|
| Buffer used | After 2 weeks | After 4 weeks |
| Buffer 1 | A | A |
| Buffer 2 | A | A ~ B |
| Buffer 3 | A | B ~ C |
| Buffer 4 | A | D |

As a result of the above experiment, no odor generated after storing for four weeks at 50° C. when using a disodium hydrogenphosphate-citric acid buffer, while no appreciable increase in the effect was seen in the combined use of the potassium dihydrogenphosphate-disodium hydrogenphosphate buffer and allantoin. In addition, when allantoin was used together, the effect was either accelerated or suppressed according to the type of buffer.

Experimental Example 3
<Confirmation of the Effect of the Combined use of a Buffer and Allantoin>

Using the disodium hydrogenphosphate-citric acid buffer (Buffer 1) which exhibited the highest effect in the combined use with allantoin, the pH stability and generation of ammonia odor were examined in the same manner as in the Experimental Example 1 to compare the effect of the independent use of allantoin and the combined use of a buffer and allantoin. A urea solution containing neither allantoin nor a buffer was used as a control. In this experiment, the pH of the urea solutions was 6.0.

(1) Preparation of Urea Solutions

The urea solutions 1–4 containing 1,3-butylene glycol (3.0%), methyl paraoxybenzoate (0.1%), and balance ion exchanged water, in addition to urea, allantoin, and Buffer 1 shown in the following Table 9, were prepared.

TABLE 9

| | Components (w/w %) | | |
|---|---|---|---|
| Urea solution | Urea | Allantoin | Buffer 1 |
| Urea solution 1 | 5.0 | 0.2 | 2.0 |
| Urea solution 2 | 5.0 | 0.2 | 0 |
| Urea solution 3 | 5.0 | 0 | 2.0 |
| Urea solution 4 | 5.0 | 0 | 0 |

(2) The Results

The pH changes when stored at 40° C. and 50° C. are respectively shown in Tables 10 and 11. The results of odor generation evaluation at 40° C. and 50° C. are shown in Tables 12 and 13.

TABLE 10

| | pH change when stored at 40° C. (Δ pH) | |
|---|---|---|
| Urea solution used | After 2 weeks | After 4 weeks |
| Urea solution 1 | 0.35 | 0.62 |
| Urea solution 2 | 1.58 | 1.56 |
| Urea solution 3 | 0.33 | 0.60 |
| Urea solution 4 | 1.91 | 2.08 |

TABLE 11

| | pH change when stored at 50° C. (Δ pH) | |
|---|---|---|
| Urea solution used | After 2 weeks | After 4 weeks |
| Urea solution 1 | 0.96 | 1.45 |
| Urea solution 2 | 1.81 | 2.15 |
| Urea solution 3 | 0.94 | 1.48 |
| Urea solution 4 | 2.34 | 2.53 |

TABLE 12

| | Ammonia odor when stored at 40° C. | |
|---|---|---|
| Urea solution used | After 2 weeks | After 4 weeks |
| Urea solution 1 | A | A |
| Urea solution 2 | A | A |
| Urea solution 3 | A | A |
| Urea solution 4 | A | A |

TABLE 13

| | Ammonia odor when stored at 50° C. | |
|---|---|---|
| Urea solution used | After 2 weeks | After 4 weeks |
| Urea solution 1 | A | A |
| Urea solution 2 | A | B ~ C |
| Urea solution 3 | A ~ B | A ~ B |
| Urea solution 4 | A ~ B | B ~ C |

The above results indicate that no difference was seen in the pH stability between the cases where a buffer was used independently and where the buffer was used in combination with allantoin. However, the ammonia odor was suppressed better by the combined use of allantoin. The effect of suppressing the odor generation from the urea solution using allantoin alone was equivalent to that of using neither allantoin nor a buffer. These results indicate that the increase in the effect by the combined use with allantoin is due to the synergistic effect of the combined use with a buffer.

Experimental Example 4
<The Effect of the Buffer Concentration>

The pH stability and generation of ammonia odor were examined in the same manner as in the Experimental Example 1 using urea solutions with a different concentration of the disodium hydrogenphosphate-citric acid buffer (Buffer 1) in which allantoin was used in combination. A urea solution which does not contain a buffer was used as a control. In this experiment, the pH of the urea solutions was 6.0.

(1) Preparation of the Urea Solutions

The urea solutions 5–8 containing 1,3-butylene glycol (3.0%), methyl paraoxybenzoate (0.1%), and balance ion exchanged water, in addition to urea, allantoin, and Buffer 1 shown in the following Table 14, were prepared.

TABLE 14

| Urea solution used | Components (w/w %) | | |
|---|---|---|---|
| | Urea | Allantoin | Buffer 1 |
| Urea solution 5 | 5.0 | 0.2 | 1.0 |
| Urea solution 6 | 5.0 | 0.2 | 2.0 |
| Urea solution 7 | 5.0 | 0.2 | 3.0 |
| Urea solution 8 | 5.0 | 0.2 | 0 |

(2) The Results

The pH changes when stored at 40° C. and 50° C. are respectively shown in Tables 15 and 16. The results of odor generation evaluation at 40° C. and 50° C. are shown in Tables 17 and 18.

TABLE 15

| | pH change when stored at 40° C. (Δ pH) | |
|---|---|---|
| Urea solution used | After 2 weeks | After 4 weeks |
| Urea solution 5 | 0.61 | 0.97 |
| Urea solution 6 | 0.35 | 0.62 |
| Urea solution 7 | 0.30 | 0.49 |
| Urea solution 8 | 1.58 | 1.56 |

TABLE 16

| | pH change when stored at 50° C. (Δ pH) | |
|---|---|---|
| Urea solution used | After 2 weeks | After 4 weeks |
| Urea solution 5 | 1.33 | 1.82 |
| Urea solution 6 | 0.96 | 1.45 |
| Urea solution 7 | 0.78 | 1.20 |
| Urea solution 8 | 1.81 | 2.15 |

TABLE 17

| | Ammonia odor when stored at 40° C. | |
|---|---|---|
| Urea solution used | After 2 weeks | After 4 weeks |
| Urea solution 5 | A | A |
| Urea solution 6 | A | A |
| Urea solution 7 | A | A |
| Urea solution 8 | A | A |

TABLE 18

| | Ammonia odor when stored at 50° C. | |
|---|---|---|
| Urea solution used | After 2 weeks | After 4 weeks |
| Urea solution 5 | A ~ B | B ~ C |
| Urea solution 6 | A | A |
| Urea solution 7 | A | A |
| Urea solution 8 | A | B ~ C |

The above results indicate that urea can be maintained stable if a buffer is used in an amount of 20% or more of the urea (or 1.0% or more of the total urea solution).

Experimental Example 5
<The Effect of pH>

Urea solutions with the same concentrations of urea, allantoin, and disodium hydrogenphosphate-citric acid buffer (Buffer 1), but having a different pH, were prepared. The pH stability and generation of ammonia odor were examined in the same manner as in the Experimental Example 1 using these urea solutions.

(1) The Composition and pH of the Urea Solutions

The urea solutions 9–11, containing urea (5.0%), allantoin (0.2%), disodium hydrogenphosphate-citric acid buffer (Buffer 1) in a 2.0% concentration, with a pH shown in the following Table 19, were prepared.

TABLE 19

| Urea solution | Measured pH (Target pH) |
|---|---|
| Urea solution 9 | 4.96 (5) |
| Urea solution 10 | 5.92 (6) |
| Urea solution 11 | 7.28 (7) |

(2) The Results

The pH changes when stored at 40° C. and 50° C. are respectively shown in Tables 20 and 21. The results of the odor generation evaluation at 40° C. and 50° C. are shown in Tables 22 and 23.

TABLE 20

| | pH change when stored at 40° C. (Δ pH) | |
|---|---|---|
| Urea solution used | After 2 weeks | After 4 weeks |
| Urea solution 9 | 0.53 | 0.95 |
| Urea solution 10 | 0.35 | 0.62 |
| Urea solution 11 | 0.25 | 0.39 |

TABLE 21

| | pH change when stored at 50° C. (Δ pH) | |
|---|---|---|
| Urea solution used | After 2 weeks | After 4 weeks |
| Urea solution 9 | 1.55 | 2.20 |
| Urea solution 10 | 0.96 | 1.45 |
| Urea solution 11 | 0.59 | 1.05 |

TABLE 22

| | Ammonia odor when stored at 40° C. | |
|---|---|---|
| Urea solution used | After 2 weeks | After 4 weeks |
| Urea solution 9 | A | A |
| Urea solution 10 | A | A |
| Urea solution 11 | A | A |

TABLE 23

| | Ammonia odor when stored at 50° C. | |
|---|---|---|
| Urea solution used | After 2 weeks | After 4 weeks |
| Urea solution 9 | A | A |
| Urea solution 10 | A | A |
| Urea solution 11 | A ~ B | B ~ C |

The above results indicate that urea can be maintained stable when the solution has a pH of 6.5 or less.

Example 1

<Preparation of a Cosmetic Composition Containing Urea>

A cosmetic composition containing urea was prepared according to the following formulation.

| (Component) | (%) |
|---|---|
| Lactic acid bacterium culture supernatant | 5 |
| Polyethylene glycol mono-stearate | 0.1 |
| γ-oryzanol | 0.01 |
| Hinokitiol | 0.001 |
| Dipotassium glycyrrhizinate | 0.1 |
| Disodium edetate | 0.1 |
| Allantoin | 0.2 |
| Urea | 3 |
| Concentrated glycerin | 5 |
| Sodium hyaluronate | 0.05 |
| Disodium hydrogenphosphate | 1 |
| Citric acid | 0.7 |
| Fatty acid monoglyceride | 1 |
| Purified water | Balance |

Example 2

<Study of Anti-atopy Effect>

The cosmetic composition containing urea prepared in Example 1 was applied to 36 subjects suffering from atopic disease (mostly atopic dermatitis, acute eczema, or dermatitis seborrheica) continuously in a usual dose twice a day. Two, four, and seven weeks after the start of application, the skin conditions in terms of dryness, scaling, erubescence, and itch sensation were examined. The results were classified into five categories according to the symptoms, i.e. heavy, medium, light, slight, and none. (Among the 36 subjects, the initial overall symptoms for 30 subjects were light and for 6 subjects slight.) The results are shown in Tables 24–27.

(Dry Skin)

TABLE 24

| | % of the subjects | | |
|---|---|---|---|
| | Light | Slight | None |
| Start | 16.7 | 83.3 | 0 |
| After two weeks | 5.3 | 73.7 | 21.0 |
| After four weeks | 0 | 30.4 | 69.6 |
| After seven weeks | 0 | 12.5 | 87.5 |

(Scaling)

TABLE 25

| | % of the subjects | | |
|---|---|---|---|
| | Light | Slight | None |
| Start | 13.9 | 83.3 | 2.8 |
| After two weeks | 5.3 | 26.3 | 68.4 |
| After four weeks | 0 | 35.3 | 64.7 |
| After seven weeks | 0 | 12.5 | 87.5 |

(Erubescence)

TABLE 26

| | % of the subjects | | |
|---|---|---|---|
| | Light | Slight | None |
| Start | 5.6 | 83.3 | 11.1 |
| After two weeks | 0 | 57.9 | 42.1 |
| After four weeks | 0 | 30.4 | 69.6 |
| After seven weeks | 0 | 25.0 | 75.0 |

(Itch Sensation)

TABLE 27

| | % of the subjects | | |
|---|---|---|---|
| | Light | Slight | None |
| Start | 5.6 | 83.3 | 5.6 |
| After two weeks | 0 | 42.1 | 57.9 |
| After four weeks | 0 | 8.7 | 91.3 |
| After seven weeks | 0 | 12.5 | 87.5 |

According to the present invention, the problems of urea-containing cosmetic composition such as pH increase and odor generation associated with the decomposition of urea, which is useful for preventing rough dry skin and maintaining moisturization, can be avoided.

Obviously, numerous modifications and variations of the present invention are possible in light of the above teachings. It is therefore to be understood that within the scope of the appended claims, the invention may be practiced otherwise than as specifically described herein.

What is claimed is:

1. A cosmetic composition for skin use which comprises urea, allantoin, and a buffer comprising disodium hydrogenphosphate and citric acid, which composition has a pH of from 6.5 to 4.5.

2. The cosmetic composition according to claim 1, wherein the amount of the buffer is from 20 w/w % to 50 w/w % of the amount of urea.

3. A method for suppressing ammonia odor of a urea containing cosmetic composition comprising adding allantoin and adjusting the pH of said composition from 6.5 to 4.5 by using a buffer comprising disodium hydrogenphosphate and citric acid.

* * * * *